(12) United States Patent
Heacock et al.

(10) Patent No.: US 8,388,131 B2
(45) Date of Patent: Mar. 5, 2013

(54) DISPOSABLE OPHTHALMIC/MEDICAL APPARATUS WITH TIMED COLOR CHANGE INDICATION

(76) Inventors: Gregory Lee Heacock, Auburn, WA (US); Louise Ellen Culham, Auburn, WA (US)

( * ) Notice: Subject to any disclaimer, the term of this patent is extended or adjusted under 35 U.S.C. 154(b) by 611 days.

(21) Appl. No.: 12/504,107

(22) Filed: Jul. 16, 2009

(65) Prior Publication Data

US 2009/0303440 A1 Dec. 10, 2009

Related U.S. Application Data

(63) Continuation of application No. 11/607,298, filed on Nov. 30, 2006, now abandoned.

(51) Int. Cl.
*G02C 7/00* (2006.01)
*G02C 7/02* (2006.01)

(52) U.S. Cl. .......... 351/159.28; 351/159.02; 351/159.24

(58) Field of Classification Search .............. 351/160 R, 351/219, 159.01, 159.02, 159.24–159.32; 600/300, 323; 435/4
See application file for complete search history.

(56) References Cited

U.S. PATENT DOCUMENTS

| | | |
|---|---|---|
| 3,899,295 A | 8/1975 | Halpern |
| 4,098,577 A | 7/1978 | Halpern |
| 4,526,752 A | 7/1985 | Perlman et al. |
| 5,159,360 A | 10/1992 | Stoy et al. |
| 5,942,438 A | 8/1999 | Antonoplos et al. |
| 6,060,210 A | 5/2000 | Eda et al. |
| 6,114,509 A | 9/2000 | Olsen et al. |
| 6,132,086 A | 10/2000 | Henwood |
| 6,218,189 B1 | 4/2001 | Antonoplos et al. |
| 6,518,231 B2 | 2/2003 | Appel et al. |
| 6,634,747 B1 | 10/2003 | Atkins et al. |
| 6,790,411 B1 | 9/2004 | Read |
| 6,851,808 B2 | 2/2005 | Heacock |
| 7,219,799 B2 | 5/2007 | Bonnette et al. |
| 7,244,252 B2 | 7/2007 | Berndt |
| 2002/0023642 A1* | 2/2002 | Holmsten et al. ........ 128/203.12 |
| 2004/0180391 A1* | 9/2004 | Gratzl et al. .................... 435/14 |
| 2005/0041200 A1 | 2/2005 | Rich |
| 2006/0054525 A1 | 3/2006 | Dean et al. |
| 2006/0069305 A1 | 3/2006 | Couvillon, Jr. et al. |
| 2006/0181676 A1 | 8/2006 | Tucker et al. |
| 2007/0017042 A1 | 1/2007 | Cincotta et al. |

OTHER PUBLICATIONS

Extended Supplementary European Search Report, EP Application No. EP07864168, Mar. 1, 2011.
The international Search Report and Written Opinion corresponding to International Application Serial No. PCT/US2007/84186 mailed Sep. 2, 2008.
Michael Freemantle, Intelligence Ink Detects Oxygen, Chemical Gas Sensing, Aug. 2, 2004, p. 11, vol. 82, No. 31, Chemical & Engineering News, USA.
International Search Report corresponding to International Application Serial No. PCT/US2007/84186, mailed Sep. 2, 2008, 2 pages.
Written Opinion of the International Searching Authority corresponding to International Application Serial No. PCT/US2007/84186, mailed Sep. 2, 2008, 12 pages.
Notification Concerning Transmittal of International Preliminary Report on Patentability, PCT/US2007/084186, mailed Jun. 11, 2009, 12 pages.

* cited by examiner

*Primary Examiner* — James Greece
(74) *Attorney, Agent, or Firm* — McAndrews, Held & Malloy Ltd.

(57) ABSTRACT

A disposable ophthalmic or medical apparatus has a portion with a color changeable dye disposed thereon. The dye changes color after being exposed to oxygen for a controlled and predetermined period of time indicating that the apparatus should no longer be used.

63 Claims, 7 Drawing Sheets

DISPOSABLE OPHTHALMIC/MEDICAL APPARATUS WITH TIMED COLOR CHANGE INDICATION

CROSS-REFERENCE TO RELATED APPLICATIONS

This application is a continuation of U.S. patent application Ser. No. 11/607,298 entitled "DISPOSABLE OPHTHALMIC/MEDICAL APPARATUS WITH TIMED COLOR CHANGE INDICATION" filed Nov. 30, 2006.

STATEMENT REGARDING FEDERALLY SPONSORED RESEARCH OR DEVELOPMENT

N/A

FIELD OF THE INVENTION

The present invention relates to a disposable, limited or restricted use product that can transmit contaminants, and disease to a person or cause infection if reused or used beyond a recommended period of time and more particularly to such an apparatus with a portion having a color changeable dye that changes color after being exposed to oxygen for a predetermined period of time indicating that the device should no longer be used.

BACKGROUND OF THE INVENTION

Many products currently marketed and sold to consumers are designed for limited use. These products are usually associated with a single event, a restricted time period or restricted access. There are many reasons for the need of single use or limited use products.

An example of a single use product is a disposable syringe. Instrument contamination and cross infection between patients is an ever present concern if the syringe is inadvertently reused. It is a particular concern in some countries where repeated use of instruments is known to transmit serious diseases such as HIV and hepatitis. Medical and ophthalmic devices that must be sterilized such as scalpels or tonometers (for the measurement of a patient's intraocular pressure) body piercing and tattooing instruments used on multiple clients also give cause for concern. Needles used in acupuncture offer another example. Decontamination procedures or employment of single-use devices are methods used to control cross infection, but they rely on personnel awareness, willingness to follow protocol, monitoring and documentation.

The limited use type of product is usually associated with goods that should be used for a restricted time period. One example of this type of product is "daily wear" or disposable contact lenses. Contact lenses for refractive correction or cosmetic purposes require suitable wear and care regimes in order to maintain good eye health. Non-compliance on the part of the patient, either through choice or due to lack of education, can injure the eye. Frequent replacement lenses are sometimes worn for longer than recommended or they may be stored or cleaned inappropriately.

A number of patents have tried to address the requirements for single use, limited use, or restricted access products.

U.S. Pat. No. 3,899,295 describes the use of an indicator containing a pH sensitive dye applied to the container of a product such as a medical instrument. The indicator displays a first color in a normal atmosphere, then following introduction of a basic atmosphere the sensor displays a second color. The problem with this patent is that the indicator is not displaying information relating to the condition of the product contained within the package. Since the indicator is not incorporated within or fixed onto the product, the information given actually relates to the container, not its contents. An additional problem with this patent is that the basic atmosphere in which the product is stored is chlorine gas which is highly reactive to the materials that comprise many of the products that one could imagine being supplied in a sterile package container, such as metal surgical instruments and many pharmaceutical compounds or drugs.

Similarly, U.S. Pat. No. 4,098,577 by the same inventor describes a similar pH sensitive indicator and two different atmospheric conditions, however that invention describes the indicator change in the presence of an acidic atmosphere. As described above, the indicator is not incorporated within or fixed onto the product, therefore the information presented by the indicator relates to the container, not its contents.

U.S. Pat. No. 4,526,752 presents a tamper resistant package with an indicator means. The invention describes a container which incorporates an indicator within its structure to display information on whether a container has been previously opened. As with other patents, the indicator relates to the condition of the package and not the product contained in the package.

U.S. Pat. No. 6,790,411 describes a solution based hydrogen peroxide indicator where the solution has a first color in normal atmospheric conditions, then following a sterilization process using hydrogen peroxide, the solution exhibits a second color. One will certainly recognize a problem with this technique by considering the case where a package that has been sterilized with hydrogen peroxide, is subsequently tampered with, punctured, or otherwise damaged and made non sterile, while the indicator still displays the sterile condition.

U.S. Pat. No. 6,851,808 describes an ophthalmic lens product with an attached indication means that provides the user information relating to the products condition or previous use. The invention overcomes many of the problems with the previously described patents. However, since the indicator means described in the patent uses changes in the product's light environment as the initiator for the use indication display, and since variations exist in the lighting environment where the product is used, the use indication can present at a rate that is faster or slower than that which is optimally desired.

BRIEF SUMMARY OF THE INVENTION

In accordance with the present invention the disadvantages of prior limited use or restricted use products that can harm a person if improperly used as discussed above have been overcome. A disposable limited or restricted use apparatus in accordance with the present invention includes a color changeable portion wherein the time that the color change occurs is controlled so that it coincides to the approximate time of the end of one use of a single use apparatus or to the approximate expiration time for extended but limited or restricted use apparatus.

More particularly, the apparatus of the present invention with color change indication of use or expiration includes a limited or restricted use apparatus having a portion that comes in contact with bodily fluids or tissue so as to be susceptible to the transmission of contaminants or disease to a person or to cause infection or injury. A color changeable dye is disposed directly on a portion of the apparatus, the dye having a first color upon immediate exposure to oxygen and for a predetermined time thereafter and the dye changing color after the predetermined time to provide a warning indication that the apparatus should no longer be used.

In one embodiment of the present invention, the apparatus may be a medical device such as a disposable syringe wherein the predetermined period of time prior to color change is approximately five minutes. In another embodiment, the medical device is a disposable scalpel and the predetermined period of time before which the dye changes color is greater than or equal to one-half hour and preferably one hour. In still another embodiment, the apparatus is an ophthalmic device such as a disposable tonometer and the predetermined period of time before the color change occurs is approximately ten minutes.

In accordance with a further feature of the invention, the position of the dye on the device may be such that the device becomes unusable after the color change occurs.

In accordance with another feature of the present invention, the apparatus is a contact lens that is intended to be worn by a user such that the lens has a peripheral area that extends beyond the pupil and/or the iris of a user's eye when worn and wherein the contact lens is disposable such that it is not intended to be used for more than a predetermined period of time. A color changeable dye is disposed on a portion of the peripheral area of the contact lens wherein the dye is somewhat translucent prior to use of the contact lens and the dye changes to a visible color after the contact lens has been exposed to oxygen for a predetermined period of time indicating that the contact lens should no longer be used. Because the color change indication of expiration is in the periphery of the lens, it does not obstruct the optical zone of the lens. As such, the lens can still be used without obstructing vision after the color change occurs. However, a user is discouraged from continuing to wear the expired contact lens since the color change indication is visible and apparent to others.

These and other advantages and novel features of the present invention, as well as details of an illustrated embodiment thereof will be more fully understood from the following description and the drawings.

DETAILED DESCRIPTION OF THE INVENTION

In accordance with the present invention, a color change indication on a product provides accurate information or a warning to a user of: prior use of a single use product or instrument; a reminder that a limited use product has reached it's expiration time; or that a product that is restricted for use has been tampered with. The warning indication is provided by a dye that changes color in a time controlled manner wherein the dye is disposed on the product itself by being either printed on the product or incorporated within the material forming a portion of the product. The product is then subsequently packaged to provide a sterile environment for the product or limited access thereto. The internal atmosphere of the package is an inert gas or a vacuum such that the package provides a sealed, substantially atmospheric oxygen free environment for the product. When the package is subsequently opened and the product is exposed to atmospheric oxygen, the dye disposed on the product will change from translucent or somewhat translucent, i.e. a milky white or "water white," to a blue or red color after a period of time that is controlled by the composition of the dye as discussed in detail below, and that is selected to correspond to the typical time for a single use of a product in the case of single use products or that corresponds to the expiration time of the product. The time at which the dye changes color can also be selected so as to indicate that the product may have been tampered with.

Figure 1:
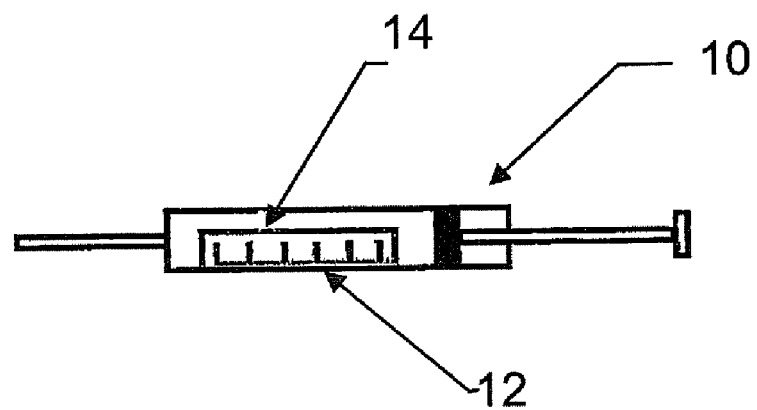
FIG. 1 is a perspective view of a syringe in accordance with one embodiment of the present invention depicting the area of the color changeable dye overlying the graduated scale of the syringe.
Figure 2:
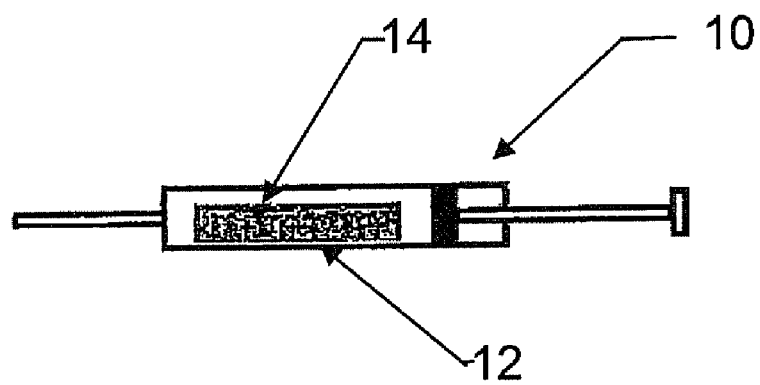
FIG. 2 is a perspective view of the syringe of FIG. 1 depicting the syringe after the timed color change occurs.

In accordance with one embodiment of the present invention, as shown in FIG. 1, a disposable syringe 10 includes a graduated scale 12 printed thereon so that the amount of liquid drawn into the syringe can be accurately measured. In one embodiment, the color changeable dye 14 is printed over the scale. In this embodiment, the dye is substantially translucent so that the scale is clearly visible until the dye 14 changes color, as depicted at 14' in FIG. 2, after a predetermined time associated with the time of typical use of the single use disposable syringe 10.

For single use disposable products where the dye is required to be substantially translucent and wherein the dye is to change color after exposure to oxygen after five to ten minutes, the dye solution may be formed as follows. Approximately 12 grams of glucose is added to 600 cc of distilled de-ionized water. Next, approximately 12 grams of sodium hydroxide is added to the mixture. To this mixture is added 10 cc of a Methylene Blue solution prepared by mixing 0.1 gram of Methylene Blue in 100 cc of ethanol where the ethanol evaporates in the drying process. Thereafter, 60 grams of methyl cellulose is added to the mixture. Alternatively, E414 acacia gum may be substituted for the methyl cellulose. This dye solution will change from translucent to blue in a short amount of time after the package is opened and the product on which the dye is disposed is exposed to oxygen. If the color change desired is from substantially translucent to a red color, 10 cc of a Safranine T solution can be substituted for the Methylene Blue solution. The Safranine T solution is prepared by mixing 0.3 grams of Safranine T with 10 ml of ethanol.

In order to delay the time at which the dye changes color upon exposure to oxygen, Iron (II) carbonate can be added to the above dye solution. For example, 0.1 grams of Iron (II) carbonate can be added to a 3 ml quantity of the above dye solution forms a dye that will change color to either blue or red after approximately nine or ten minutes. By increasing or decreasing the amount of Iron (II) carbonate the time that it takes for the color change to occur upon exposure to oxygen can be respectively increased or decreased. It is noted that, the addition of the Iron (II) carbonate will change the dye from being substantially translucent to somewhat translucent or a faint, milky white known as "water white" wherein the translucency diminishes as more Iron (II) carbonate is added.

In a preferred embodiment of the disposable syringe, a dye is employed that remains translucent or somewhat translucent for a period of approximately five minutes, the typical time of a single use of the disposable syringe. In the embodiment of the syringe depicted in FIGS. 1 and 2, because the dye is disposed over the graduated scale, when the time controlled color change occurs, the graduated scale is no longer clearly visible so that the disposable syringe cannot be accidentally reused. In this manner, the transmission of contaminants or disease from one patient to another by an inadvertent reuse of the syringe is prevented.

Figure 3:
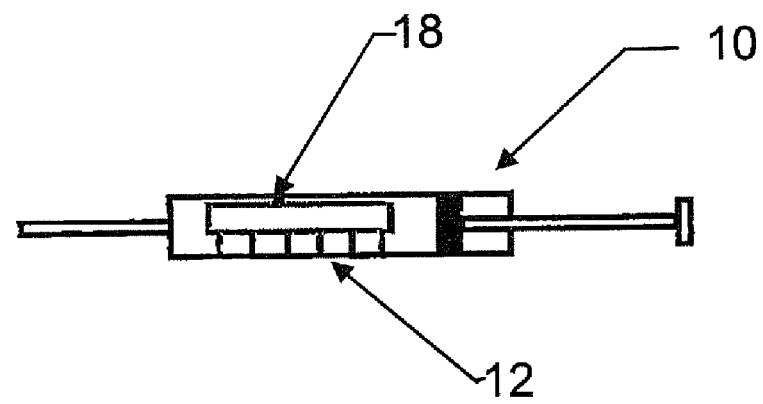
FIG. 3 is an illustration of an alternative placement of the dye on a syringe.
Figure 4:
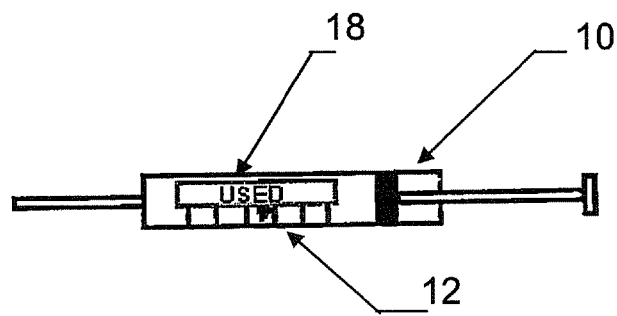
FIG. 4 is an illustration of the syringe of FIG. 3 with an expiration message printed with the color changeable dye which becomes visible after a predetermined period of time.
Figure 5:
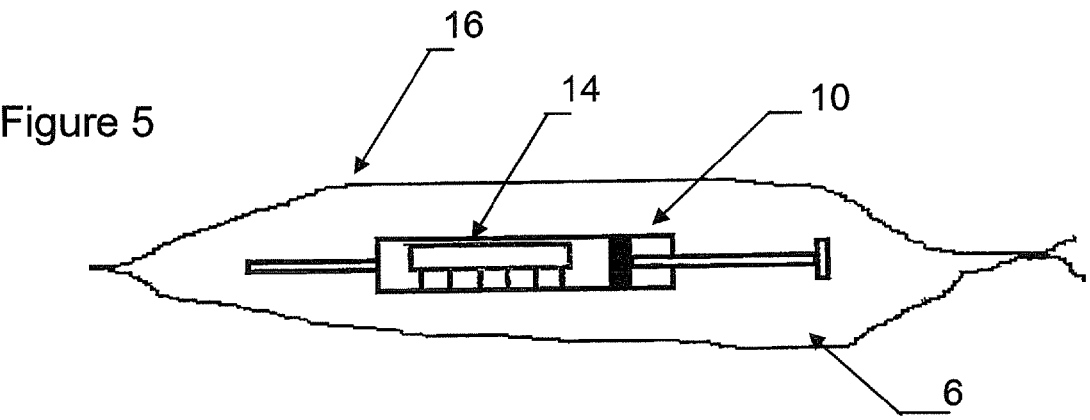
FIG. 5 is a perspective view of the syringe of FIG. 3 contained in a package to prevent premature actuation of the color changeable dye.

In another embodiment of the present invention as depicted in FIGS. 3 and 4, the dye is disposed on another area such as 18 of the disposable syringe 10. The dye can be used as an ink to print a message on the disposable product so that when the color change occurs the message, such as the word "USED," becomes visible to the user as shown at 18' in FIG. 4. The dye of the present invention dries quickly after placed on the product. After it is dry, the product can be sterilized with any common, low temperature sterilization technique and then placed in a sealed container or package 16, as depicted in FIG. 5, with an internal atmosphere of an inert gas or a vacuum. In the sealed, substantially atmospheric oxygen free package, the ink will remain translucent or "water white". When the package is subsequently opened and the product is exposed to atmospheric oxygen, the dye disposed on the product will change from substantially translucent or "water white" to blue or red after five or ten minutes depending upon the amount of Iron (II) carbonate in the solution.

If it is desired that the color change takes substantially longer than ten minutes, for example, twelve to sixteen hours, 0.5 grams of Iron (II) carbonate is added to a 3 ml quantity of the dye solution instead of 0.1 grams of Iron (II) carbonate. It is noted that the Iron (II) carbonate acts as an oxygen scavenger in the dye solution that preferentially absorbs oxygen, converting to Iron (III) carbonate. When the Iron (II) carbonate is completely converted to Iron (III) carbonate, the oxygen in the environment reacts with the color changeable dye so that the dye changes to blue or red and becomes visible.

In order to prevent the dye from changing color until an even longer time has passed, wax can be added to the dye solution. To provide a color change indication on a product after approximately 1500 hours or about two months, the oxygen diffusion rate through the dye solution can be lowered or decreased by the addition of wax as follows. Specifically, when 0.3 cc of beeswax is added to a 3 ml quantity of the dye described above, the color change is delayed by approximately ten hours for a volume of dye of 0.01 mm3. This amount of dye can be used in an area of approximately 2 mm in height and 20 mm long on a product. With the addition of 0.6 cc beeswax to the dye solution, the color change can be delayed to approximately 100 hours. To further extend the time that it takes for the color change to 1500 hours, 0.7 grams of Iron (II) carbonate can be added to the dye solution and wax mixture. It is noted that if too much wax is added to the dye, the quality of printing text can decrease.

Figure 6:
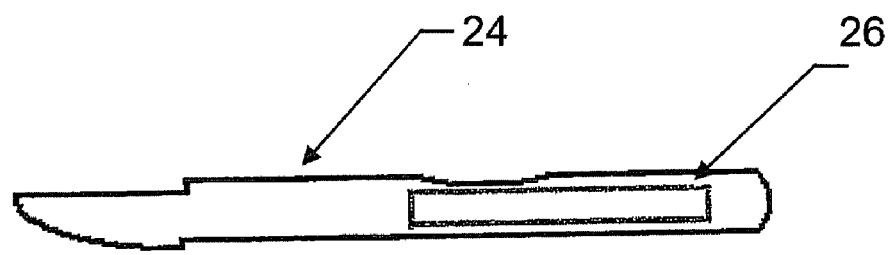
FIG. 6 is a perspective view of a scalpel with the color changeable dye in accordance with another embodiment of the present invention.
Figure 7:
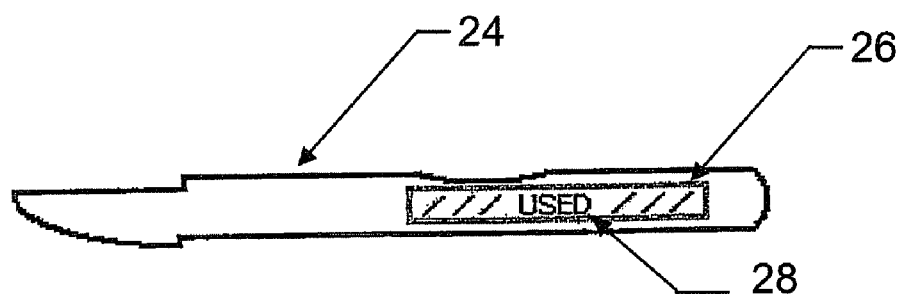
FIG. 7 is a perspective view of the scalpel of FIG. 6 with a message printed with the color changeable dye which has become visible after a predetermined time.

In another embodiment of the present invention as depicted in FIG. 6, a disposable scalpel 24 has the dye 26 of the present invention disposed thereon in an area that will be clearly visible to the surgeon when the dye changes color. As depicted in FIG. 7, a warning message 28 may be printed with the dye on the scalpel to inform the surgeon that the scalpel has been "USED" wherein the color change occurs after at least one-half hour and preferably one hour after the scalpel is removed from a substantially oxygen free package or container as discussed above with respect to the syringe. In this way, the surgeon is warned that the scalpel should not be inadvertently used again but should be disposed of.

Figure 8:
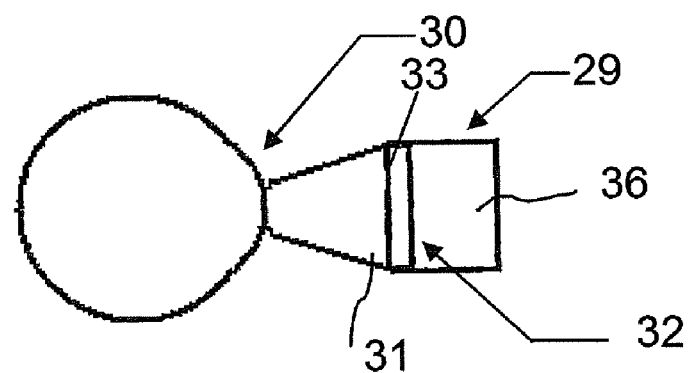
FIG. 8 is a cross-sectional view of a tonometer contacting a user's eye and having the color changeable dye disposed on a central area of the tonometer lens through which the clinician looks.
Figure 9:
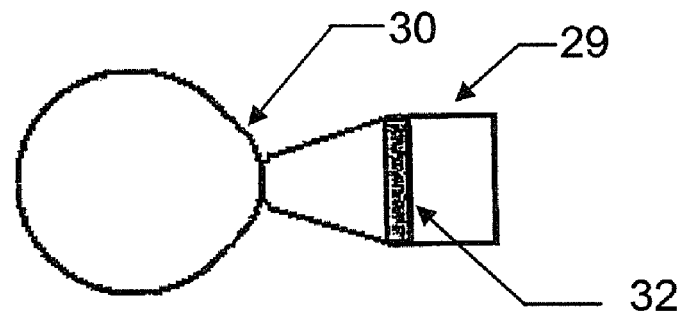
FIG. 9 is a cross-sectional view of the tonometer and eye of FIG. 8 with the dye providing a color change indication that the tonometer should no longer be used.

An ophthalmic device that incorporates the present invention is depicted in FIGS. 8 and 9. Specifically, FIG. 8 illustrates a tonometer 29 that is used in contact with a patient's eyes 30. In ophthalmology, various procedures require a lens or instrument that contacts a patient's eye. A tonometer is one such device which includes a lens 31 which, for a disposable tonometer, may be formed of optical quality acrylic, for example. The lens 31 has a surface 33 through which a clinician views the eye 30 when the tonometer 29 is mounted on a slit lamp. The tonometer 29 also includes a holder 29 which is used to mount the tonometer onto the slit lamp. For a disposable tonometer, the holder 29 can be formed of plastic for example. In accordance with one embodiment, the dye 32 of the present invention can be disposed on a central area of the lens 31 of the tonometer. Since the typical time of use of the disposable tonometer 29 of the present invention is very short, the dye 32 can be of a formulation that is substantially translucent and does not change color for approximately five to ten minutes. After that time, when the dye changes color to blue or red, the dye prevents inadvertent reuse of the disposable tonometer by blocking the visual path in the tonometer to the patient's eye. Thus, the inadvertent transmission of contaminants or diseases from one patient to another patient via contact of a reused ophthalmic device with the patient's eyes is prevented. In another embodiment of the present invention, the dye can be disposed to form a ring or other symbol on the surface 33 of the tonometer lens 31 or the dye can be disposed on the holder of the tonometer 36.

A problem that has arisen in ophthalmology with refractive contact lens use such as "daily wear" or "monthly wear" disposable contact lenses is that the user of the contact lens does not dispose of the contact lens at the recommended time but wears the contact lens longer than they are supposed to. This however can damage the eye. The contact lens of the present invention as depicted in FIGS. 10-14 overcomes this problem by providing a visual indication on the contact lens itself that the contact lens should be removed from the eye after the contact lens has been worn for the prescribed amount of time.

Figure 10:
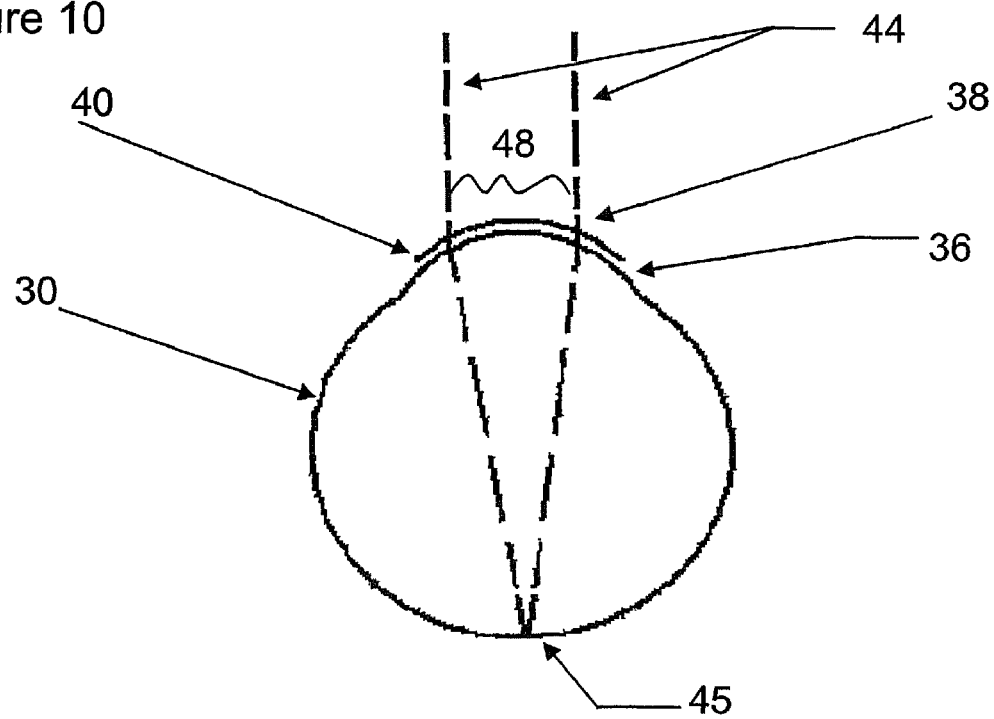
FIG. 10 is a cross-sectional view of a contact lens in accordance with another embodiment of the present invention on a user's eye.
Figure 11:
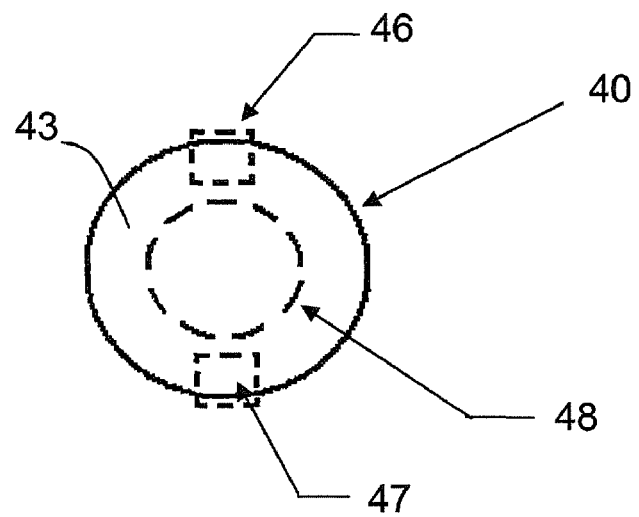
FIG. 11 is a front perspective view of the contact lens of FIG. 10 with the dye in peripheral areas of the contact lens.

As shown in FIG. 10, a refractive contact lens 40 is worn on a cornea 36 of an eye 30. Light 44 entering the person's cornea is correctly focused by the contact lens 13 onto the retina at a point 45. The clear optical path of the light 44 intersects the central portion of the contact lens in the optical zone 48 of the eye and or lens. The periphery 43 of the contact lens 40 as shown in FIGS. 10-13, however extends beyond the optical zone 48 of the user's eye such that when the contact lens is worn, the peripheral area of the contact lens extends beyond the pupil and/or iris of a user's eye so that it overlies the iris and/or the sclera.

Figure 12:
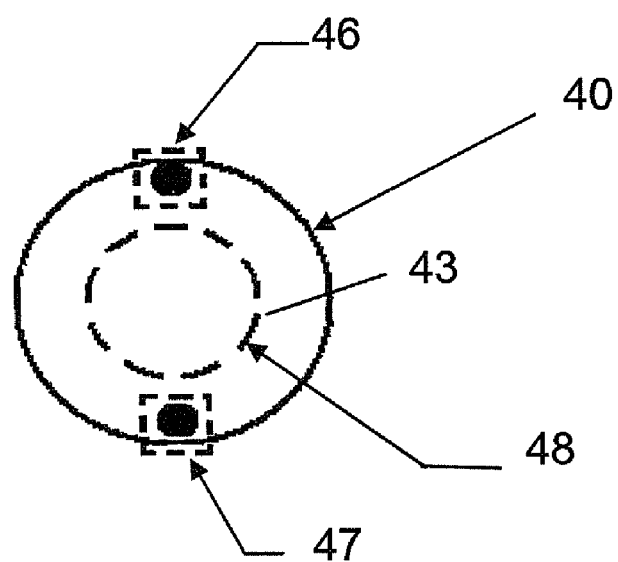
FIG. 12 is a front perspective view of the contact lens of FIG. 11 depicting the dye after color change has occurred to indicate expiration of the lens.
Figure 14:
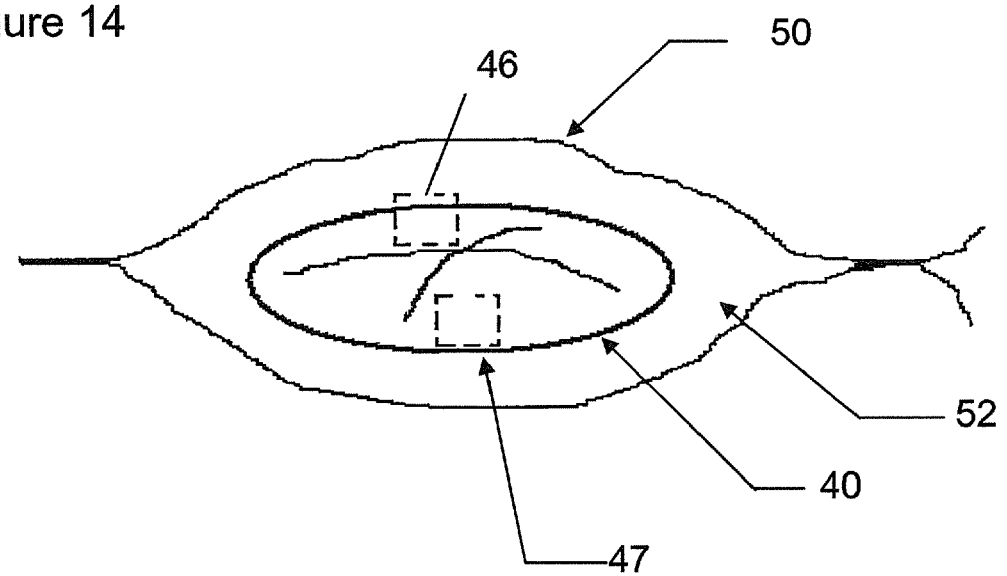
FIG. 14 is a cross-sectional view of a package containing the contact lens of FIG. 11 to prevent premature color change.

In accordance with the present invention, the color changeable dye 46 as described above is disposed on a portion of the peripheral area of the contact lens. The formulation for the dye is preferably that which delays the color change of the dye for approximately twelve to sixteen hours, or longer, according to the longest time that the contact lens manufacturer suggests that the contact lenses should be worn. Because the formulation for the dye for twelve to sixteen hours includes Iron (II) carbonate, prior to the color change, the dye is milky white or "water white". However, when the dye is disposed in one or more areas such as 46 and 47 in the periphery 43 of the contact lens 40, when the contact lens is worn by the user the area in which the dye is placed on the contact lens overlies the iris and/or the sclera and is not visible to an observer. As discussed above for the other devices, the contact lens 40 should be placed in a substantially atmospheric oxygen free package 50 as shown in FIG. 14. A user of the contact lens 40 removes the contact lens from the package for immediate use in the eye. After the contact lens has been worn in the eye for the recommended time by the manufacturer, the color change of the dye occurs as depicted in FIG. 12 wherein, dark blue or dark red spots are clearly visible in the periphery of the contact lens by an observer looking into the contact lens wearer's eye. As such, the contact lens wearer is encouraged to remove the contact lens from his eye and dispose of it as recommended. However, because the dye is disposed in the periphery of the contact lens outside of the optical zone 48, the dye, after it changes color does not impair the vision of the user. As such, in emergencies, the contact lens can be continued to be worn after the color change occurs without visual impairment. However, the user is discouraged from wearing the lens beyond its recommended use time since the die spots or ring will be readily apparent by anyone looking at the contact lens wearer's eye.

Figure 13:
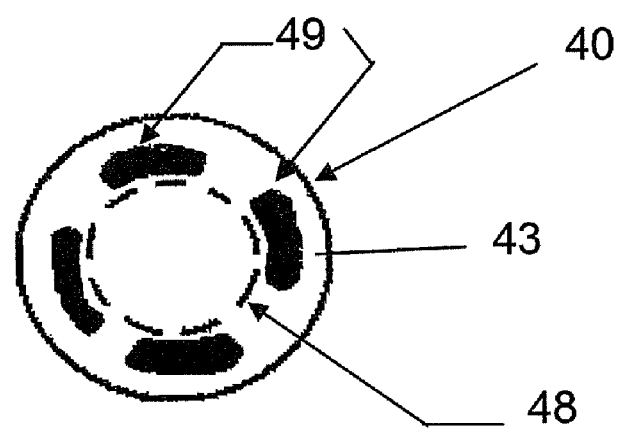
FIG. 13 is an alternative embodiment of the contact lens of FIG. 11.

FIG. 13 illustrates another embodiment of the positioning of the dye to form portions of a ring or a continuous ring in the periphery 43 of the contact lens outside the optical zone 48.

The present invention has much wider applications than have been described herein. For example, the dye of the present invention can be used on cosmetic applicators that are stored with the cosmetic itself such as mascara or eyeliner. It has been found that although such cosmetics include preservatives to slow the growth of bacteria that can infect the eye, these preservatives have a limited life so that replacement of cosmetics is recommended by doctors every three to six months. The cosmetics however do not have an expiration date on the product or the package. The dye of the present invention can be applied to the handle of a mascara applicator or eyeliner applicator, for example, so that a warning message becomes visible at the recommended time of replacement. As such a user is warned that the cosmetic should be disposed of prior to the expiration of the preservative to prevent eye infections. The present invention is also applicable to oral medications such as pills wherein the dye is printed directly onto the pill and changes color from white or translucent to another darker color or warning symbol when the environmental oxygen level around the pill changes. If the pills are individually packaged, the color change indication can occur quickly after opening the package so as to provide a tamper indication. Alternatively, if multiple pills are contained in a bottle or the like, the color change indication of the dye should be timed to coincide with the expiration of the pills. It is noted that in preparing the, Methylene Blue solution, instead of ethanol, another type of alcohol can be used wherein the alcohol evaporates on the pill in the drying process.

Many further modifications and variations of the present invention are possible in light of the above teachings. Thus, it is to be understood that, within the scope of the appended claims, the invention may be practiced otherwise than as described hereinabove.

What is claimed and desired to be secured by Letters Patent is:

1. A contact lens with expiration color change indication comprising:

a disposable contact lens to be worn by a user, the contact lens having a peripheral area that extends beyond the pupil of a user's eye, the disposable contact lens being such that the lens is not to be worn for more than a defined period of time; and an oxygen sensing color changeable dye disposed on a portion of the peripheral area of the contact lens, the dye being somewhat translucent prior to use of the contact lens and changing to a warning color after the contact lens has been exposed to atmospheric oxygen for a period of time corresponding to said defined period of time.

2. A contact lens as recited in claim 1 wherein the dye is disposed around the periphery of the contact lens to form a visible portion of at least part of a ring indicating that the contact lens should no longer be used.

3. A contact lens as recited in claim 1 wherein the dye is disposed in at least one spot in the periphery of the contact lens to form a visible symbol indicating that the contact lens should no longer be used.

4. A contact lens as recited in claim 1 wherein the dye remains somewhat translucent for at least 12 hours and thereafter changes to the warning color.

5. A contact lens as recited in claim 1 wherein the period of time that the dye is exposed to oxygen before changing color is approximately equal to the predetermined period of time.

6. A contact lens as recited in claim 1 wherein the dye comprises at least Methylene Blue, glucose, and sodium hydroxide.

7. A contact lens as recited in claim 1 wherein the dye comprises at least Safranine T, glucose and sodium hydroxide.

8. A contact lens as recited in claim 1 wherein the dye comprises at least Methylene Blue, glucose, sodium hydroxide, and Iron (II) carbonate.

9. A contact lens as recited in claim 1 wherein the dye comprises at least Safranine T, glucose, sodium hydroxide and Iron (II) carbonate.

10. A contact lens as recited in claim 1 wherein the dye comprises at least Methylene Blue and wax.

11. A contact lens as recited in claim 1 wherein the dye comprises at least Safranine T and wax.

12. A contact lens as recited in claim 1 wherein the dye comprises at least Methylene Blue, wax and Iron (II) carbonate.

13. A contact lens as recited in claim 1 wherein the dye comprises at least Safranine T, wax and Iron (II) carbonate.

14. A contact lens as recited in claim 1 wherein the dye comprises at least glucose, sodium hydroxide, Methylene Blue or Safranine T, and methyl cellulose or acacia gum.

15. A contact lens as recited in claim 14 wherein the dye further includes wax.

16. A contact lens as recited in claim 14 wherein the dye further includes Iron (II) carbonate.

17. A contact lens as recited in claim 14 wherein the dye further includes wax and Iron (II) carbonate.

18. A contact lens with expiration color change indication comprising:
- a disposable contact lens to be worn by a user; and
- an oxygen sensing color changeable dye disposed on an area of the contact lens, the dye being fairly translucent prior to use of the contact lens and for a period of time that is equal to or greater than twelve hours and the dye changing to a visible color after the contact lens has been exposed to atmospheric oxygen for said period of time indicating that the contact lens is not to be worn.

19. A contact lens as recited in claim 18 wherein the dye comprises at least Methylene Blue, glucose, sodium hydroxide, and Iron (II) carbonate.

20. A contact lens as recited in claim 18 wherein the dye comprises at least Safranine T, glucose, sodium hydroxide and Iron (II) carbonate.

21. A contact lens as recited in claim 18 wherein the dye comprises at least Methylene Blue and Iron (II) carbonate.

22. A contact lens as recited in claim 18 wherein the dye comprises at least Safranine T and Iron (II) carbonate.

23. A contact lens as recited in claim 18 wherein the dye comprises at least Methylene Blue and wax.

24. A contact lens as recited in claim 18 wherein the dye comprises at least Safranine T and wax.

25. A contact lens as recited in claim 18 wherein the dye comprises at least Methylene Blue, wax and Iron (II) carbonate.

26. A contact lens as recited in claim 18 wherein the dye comprises at least Safranine T, wax and Iron (II) carbonate.

27. A disposable ophthalmic or medical apparatus with color change indication of use comprising:
- a disposable ophthalmic or medical device having a portion that comes in contact with bodily fluids or tissue so as to be susceptible to the transmission of contaminates or disease to a patient;
- an oxygen sensing color changeable dye disposed on the device, the dye being translucent or having a first color upon immediate exposure to atmospheric oxygen and for a defined time thereafter and the dye changing color after exposure to atmospheric oxygen for the defined time indicating that the device is no longer to be used.

28. An apparatus as recited in claim 27 wherein the device is a syringe and the predetermined period of time is approximately five minutes.

29. An apparatus as recited in claim 27 wherein the device is a scalpel and the predetermined period of time is greater than or equal to one half hour.

30. An apparatus as recited in claim 27 wherein the device is a tonometer and the predetermined period of time is approximately 10 minutes.

31. An apparatus as recited in claim 27 wherein the dye is disposed on an area of the device that makes the device unusable after the dye changes color.

32. An apparatus as recited in claim 27 wherein the device includes a dispenser with a scale for measuring the amount to be dispensed and the dye is disposed over at least a portion of the scale to prevent use thereof after the dye changes color.

33. An apparatus as recited in claim 27 wherein the dye comprises at least Methylene Blue, glucose, and sodium hydroxide.

34. An apparatus as recited in claim 27 wherein the dye comprises at least Safranine T, glucose and sodium hydroxide.

35. An apparatus as recited in claim 27 wherein the dye comprises at least Methylene Blue, glucose, sodium hydroxide, and Iron (II) carbonate.

36. An apparatus as recited in claim 27 wherein the dye comprises at least Safranine T, glucose, sodium hydroxide and Iron (II) carbonate.

37. An apparatus as recited in claim 27 wherein the dye comprises at least Methylene Blue and wax.

38. An apparatus as recited in claim 27 wherein the dye further includes wax and Iron (II) carbonate.

39. An apparatus as recited in claim 27 wherein the dye comprises at least Methylene Blue, wax and Iron (II) carbonate.

40. An apparatus as recited in claim 27 wherein the dye comprises at least Safranine T, wax and Iron (II) carbonate.

41. An apparatus as recited in claim 27 wherein the dye comprises at least glucose, sodium hydroxide, Methylene Blue or Safranine T, and methyl cellulose or acacia gum.

42. An apparatus as recited in claim 27 wherein the dye further includes wax.

43. An apparatus as recited in claim 27 wherein the dye further includes Iron (II) carbonate.

44. An apparatus as recited in claim 27 wherein the dye further includes wax and Iron (II) carbonate.

45. An apparatus with time controlled color change indication comprising:
- a limited use apparatus that has a portion that comes in contact with bodily fluids or tissue and can cause harm to a person if used beyond a limited time or reused;
- an oxygen sensing color changeable dye disposed directly on a portion of the apparatus, the dye being translucent or having a first color upon immediate exposure to atmospheric oxygen and for a defined time thereafter and the dye changing color after exposure to atmospheric oxygen for the defined time indicating that the apparatus is no longer to be used.

46. An apparatus as recited in claim 45 wherein the dye comprises at least Methylene Blue, glucose, and sodium hydroxide.

47. An apparatus as recited in claim 45 wherein the dye comprises at least Safranine T, glucose and sodium hydroxide.

48. An apparatus as recited in claim 45 wherein the dye comprises at least Methylene Blue, glucose, sodium hydroxide, and Iron (II) carbonate.

49. An apparatus as recited in claim 45 wherein the dye comprises at least Safranine T, glucose, sodium hydroxide and Iron (II) carbonate.

50. An apparatus as recited in claim 45 wherein the dye comprises at least Methylene Blue and wax.

51. An apparatus as recited in claim 45 wherein the dye further includes wax and Iron (II) carbonate.

52. An apparatus as recited in claim 45 wherein the dye comprises at least Methylene Blue, wax and Iron (II) carbonate.

53. An apparatus as recited in claim 45 wherein the dye comprises at least Safranine T, wax and Iron (II) carbonate.

54. An apparatus as recited in claim 45 wherein the dye comprises at least glucose, sodium hydroxide, Methylene Blue or Safranine T, and methyl cellulose or acacia gum.

55. An apparatus as recited in claim 45 wherein the dye further includes wax.

56. An apparatus as recited in claim 45 wherein the dye further includes Iron (II) carbonate.

57. An apparatus as recited in claim 45 wherein the dye further includes wax and Iron (II) carbonate.

58. An apparatus as recited in claim 45 wherein the dye is printed on the limited use apparatus.

59. An apparatus as recited in claim 45 wherein the dye is in a material of the apparatus.

60. An apparatus as recited in claim 45 wherein the dye indicates use of the apparatus after the color change occurs.

61. An apparatus with a color change indication of use, comprising:
   a disposable ophthalmic or medical device having a portion that comes in contact with a patient's bodily fluids or tissue so as to be susceptible to the transmission of contaminates or disease to a patient;
   an oxygen sensing color changeable dye disposed on the device, the dye being translucent or having a first color upon immediate exposure to atmospheric oxygen and for a period of time thereafter wherein the period of time is five minutes or greater and the dye changing color after the device has been exposed to atmospheric oxygen for the period of time.

62. An apparatus as recited in claim 61 wherein the period of time is ten minutes or greater.

63. An apparatus as recited in claim 61 wherein the period of time is thirty minutes or greater.

* * * * *